US006863067B2

(12) United States Patent
Loncar

(10) Patent No.: US 6,863,067 B2
(45) Date of Patent: Mar. 8, 2005

(54) DEVICE FOR EXCHANGE OF GAS VOLUME

(75) Inventor: Mario Loncar, Ekerö (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/714,220

(22) Filed: Nov. 14, 2003

(65) Prior Publication Data

US 2004/0103894 A1 Jun. 3, 2004

(30) Foreign Application Priority Data

Nov. 28, 2002 (SE) ............................................... 0203519

(51) Int. Cl.⁷ ........................ A61M 15/00; A61M 16/10
(52) U.S. Cl. ............. 128/203.12; 128/910; 128/205.27; 128/205.28; 128/205.24; 128/203.18; 128/203.25; 128/205.12
(58) Field of Search ....................... 128/203.12, 203.13, 128/203.14, 203.15, 203.18, 203.22, 203.24, 203.25, 203.26, 205.12, 205.27, 910, 203.28, 204.18, 204.21, 204.22, 205.13, 205.14, 205.15, 205.24, 205.28, 912; 95/90; 96/108, 109

(56) References Cited

U.S. PATENT DOCUMENTS

2001/0022181 A1 9/2001 Mason et al.

FOREIGN PATENT DOCUMENTS

| DE | 199 55 078 | 5/2001 |
|----|------------|--------|
| WO | WO 88/07876 | 10/1988 |
| WO | WO 99/40961 | 8/1999 |
| WO | WO 00/76569 | 12/2000 |

Primary Examiner—Henry Bennett
Assistant Examiner—Andrea M. Ragonese
(74) Attorney, Agent, or Firm—Schiff Hardin LLP

(57) ABSTRACT

A device for exchanging gas volumes in an anesthetic system has an inlet, an outlet, a first chamber arranged between the inlet and the outlet, a second chamber arranged between the inlet and the outlet, a switching valve for selective connection to the first chamber or the second chamber for forming a flow path between the inlet and the outlet, and a controller for controlling the switching valve.

1 Claim, 1 Drawing Sheet

DEVICE FOR EXCHANGE OF GAS VOLUME

BACKGROUND OF THE INVENTION

1. Field of the Invention

The present invention relates to a device for exchange of gas volumes, suitable for use in an anesthetic system.

2. Description of the Prior Art

In many anesthetic systems a portion of breathing gas circulates so that it is returned to a patient. This may range from the entire breathing gas to a component in the breathing gas (anesthetic agent). The gas that is exhaled contains carbon dioxide. This is diluted in certain systems and it is filtered out in others.

Both of the variants result in certain disadvantages. In the former case there is often a large waste of fresh gas (including costly gases) and in the other case a flow resistance is introduced in the system.

In one type of anesthetic system a unit for adsorption and desorption of gaseous anesthetic is used. This results in anesthetic gas being selectively returned to the patient whilst other components in the breathing gas are replaced with every breath.

However, the unit unavoidably occupies a certain physical volume, which has the consequence that a certain amount of carbon dioxide may be stored in the unit and re-supplied to the patient with the consecutive breath. The amount of carbon dioxide does not constitute a risk to the patient but may disturb the acquisition of carbon dioxide level measurement curves (capnogram).

This amount may be easily trapped using a small absorber unit for carbon dioxide but, as mentioned above, the flow resistance may increase with every unit in the system.

A desire therefore exists to find a solution that minimizes the level of carbon dioxide without the need to use a resistance-increasing component.

SUMMARY OF THE INVENTION

An object of the present invention is to at least partially solve the above problem.

The above object is achieved in accordance for the invention in a device where exchanging gas volumes in an anesthetic system, the device having an inlet, an outlet, a first chamber disposed between the inlet and the outlet, a second chamber also disposed between the inlet and the outlet, a switching valve for selectively placing either the first chamber or the second chamber in fluid communication with the inlet and the outlet to form a flow path between the inlet and the outlet, and a controller for controlling the switching valve.

The above object also is achieved in accordance with the invention in a tubing system having a device as described immediately above, as well as in an anesthetic system having a tubing system with such a device.

By means of a gas volume exchanger the carbon dioxide-free breathing gas from the dead volume in the anesthetic system/patient can be stored at the beginning of expiration (exhalation) and re-supplied to the expiration flow during a later part of the expiration, i.e., a gas volume from the beginning of the expiration changes places with that of a later part of the expiration. The carbon dioxide-free gas volume that is thus attained comes to fill, for example, the unit for adsorption and desorption of gaseous anesthetic so that no carbon dioxide is re-supplied to the patient with the consecutive inspiration (inhalation).

DESCRIPTION OF THE PREFERRED EMBODIMENTS

Figure 1:
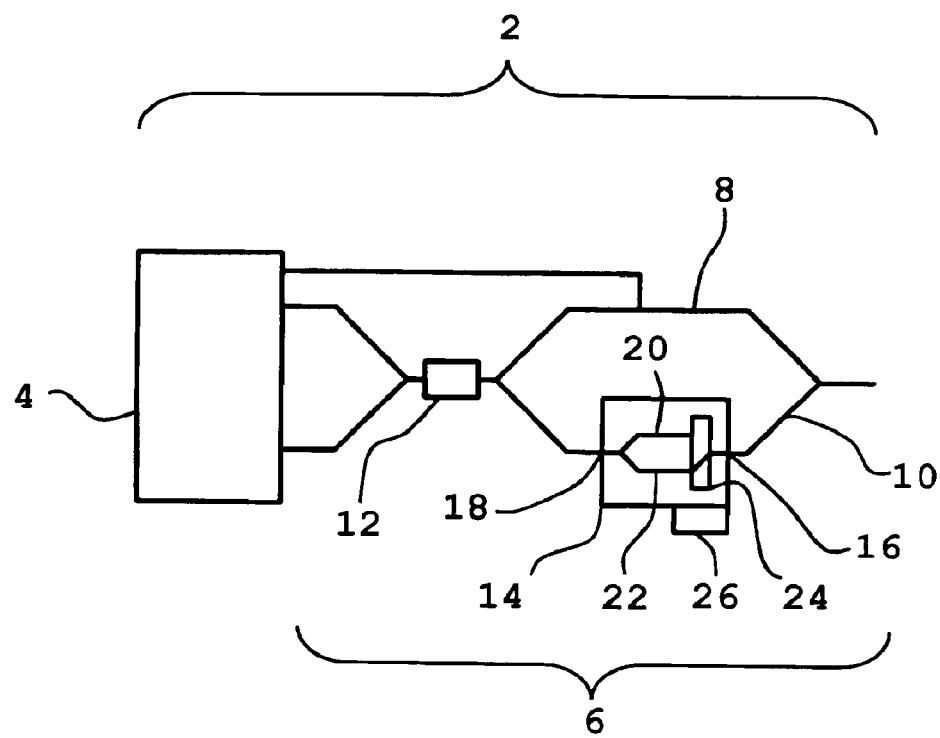
FIG. 1 schematically illustrates an anesthetic system including a tubing system with a device according to the invention.

An anesthetic system 2 according to the invention is shown schematically in FIG. 1. The anesthetic system 2 includes an anesthetic apparatus 4 and a tubing system 6. The depicted configuration is only one of many known possible configurations that can be employed.

The tubing system 6 has inter alia, an inspiration branch 8 that, in a known manner, leads breathing gas to a (not shown) patient, and an expiration branch 10 for leading (in a known manner) gas away from the patient during exhalation.

A unit 12 for adsorption and desorption of gaseous anesthetic is arranged in the tubing system 6 for adsorbing anesthetic from exhaled gas that comes from the expiration branch 10 and describing this into breathing gas that is led to the inspiration branch 8 during the consecutive inhalation.

In order to inhibit carbon dioxide in exhaled gas from collecting in the unit 12 and being re-supplied to the patient a device 14 for the exchange of gas volumes is arranged in the expiration branch 10.

The device 14 has an inlet 16 and an outlet 18 (oriented dependent on the flow direction in the expiration branch 10). A first chamber 20 and a second chamber 22 are arranged between the inlet 16 and the outlet 18. The chambers 20,22 can be exchange-coupled as flow paths in the expiration branch by means of a switching valve 24. The switching valve 24 is controlled by a controller 26.

The device 14 operates as follows: During the initial phase of expiration (exhalation) gas from the dead volume enters the tubing system 6 (that is, the volume in the common part of the inspiration branch 8 and the expiration branch 10 facing the patient, which may include a humidifier, heat/moisture exchanger, etc.) and the gas flows through the expiration branch 10. The gas has not been involved in gas exchange in the patient's lungs and is thus essentially free of carbon dioxide.

The switching valve 24 is controlled by the controller 26 so that this carbon dioxide free gas flows through the first chamber 20. (Obviously, this requires that the dead space volume first must flow to the device 14. The volume between the device 14 and the dead space contains remnants from the previous expiration and thus contains carbon dioxide.) When a volume equivalent to the dead volume has filled the first chamber 20 the switching valve 24 is controlled to switch so that the exhaled gas flows through the second chamber 22, through the outlet 18 and on to the unit 12.

Toward the end of expiration the switching valve 24 is re-set back to the previous position by the controller 26 so that gas flows again through the first chamber 20. The gas that has been stored there then flows out through the outlet 18, towards the unit 12. As the stored gas in the first chamber 20 is free from carbon dioxide this then flushes carbon dioxide from the unit 12. At the beginning of inspiration carbon dioxide-free breathing gas thus will flow through the inspiration branch 8. In other words, the device 14 moves the dead space volume in the expired gas during expiration from the beginning of the gas flow to a later portion of the exhaled gas volume or flow.

The timing of the switching is naturally of importance. The controller 26 may be formed to be directly programmed by a user or to receive proper programming from other equipment, such as the anesthetic apparatus 4. Such entering of programming or transfer of information/programming is well known per se and need not be further described herein.

Some of the relevant information helpful in calculating or determining optimum timing of the switching valve 24 includes dead space volume, expiration branch volume between the device 14 and the unit 12, expiration branch volume between the device and the dead space and tidal volume (expected exhaled volume). The timing then can be set so that essentially all of the carbon dioxide free dead space gas has reached the common part of the inspiration branch 8 and expiration branch 10 facing the unit 12 at the end of expiration. A minimum of carbon dioxide then is returned at the commencing inspiration.

When receiving information from the anesthetic apparatus 4, the controller 26 can base its control on flow values, volume calculations, or synchronize its control based on control signals for the anesthetic apparatus 4 itself.

Other possibilities are feasible. The important issue is that the controller 26 controls the timing of the switching valve 24 to achieve the gas exchanging effect. Needless to say, the controller 26 may be incorporated or fully integrated (by hardware or software) into the anesthetic apparatus 4 or other devices used in connection with the device 14.

Figure 2:
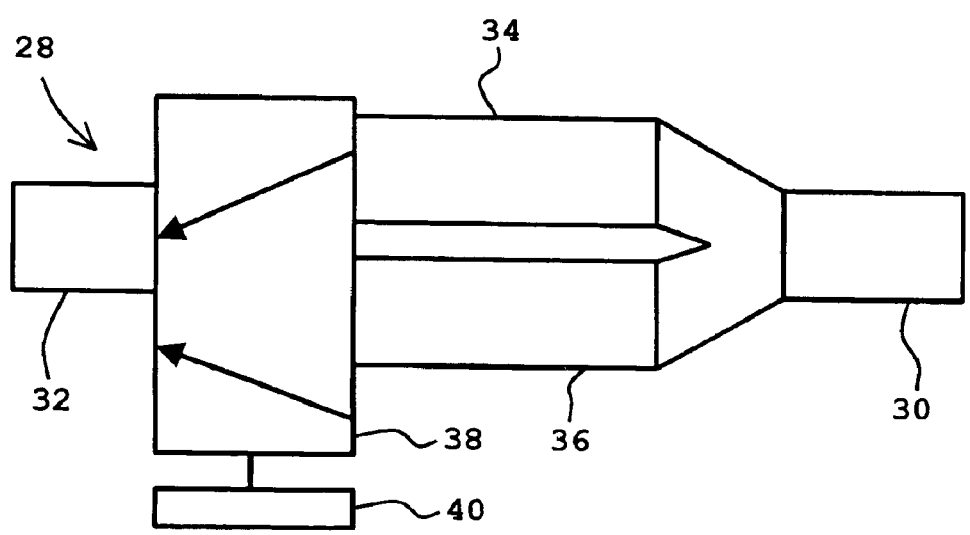
FIG. 2 shows an alternative embodiment of the device.

An alternative embodiment of a device 28 according to the invention is shown in FIG. 2. The device 28 has an inlet 30, an outlet 32, a first chamber 34, a second chamber 3, a switching valve 38 and a controller 40. In this example the switching valve 38 is arranged at the outlet 32 and not the inlet 30 of the device 28. The operation is, however, the same, with an exchange of a gas volume from the beginning of expiration to the end of expiration.

Although modifications and changes may be suggested by those skilled in the art, it is the intention of the inventor to embody within the patent warranted hereon all changes and modifications as reasonably and properly come within the scope of his contribution to the art.

I claim as my invention:

1. A tubing system for use in an anesthetic system, said tubing system comprising:

a unit for adsorption and desorption of gaseous anesthetic;

an expiration branch adapted for respiratory communication with a respirating subject, said expiration branch being disposed upstream of said unit for adsorption and desorption of gaseous anesthetic; and a gas volume exchanger connected in said expiration branch, said gas volume exchanger comprising an inlet and outlet, a first chamber disposed between the inlet and the outlet, a second chamber disposed between the inlet and the outlet, a switching valve for selectively placing one of said first chamber or said second chamber in fluid communication with said inlet and said outlet to form a flow path between said inlet and said outlet, and a controller for controlling switching of said switching valve dependent on respiration of said subject for isolating a carbon dioxide-free volume of gas in said first chamber at a beginning of expiration while allowing flow of expiratory gas through said second chamber, and for communicating said carbon dioxide-free volume of gas to said unit during a latter part of expiration, for making said carbon dioxide-free gas available during a next inspiration for flushing said unit of carbon dioxide without involvement of a carbon dioxide filter.

* * * * *